US012558032B2

(12) United States Patent
Nadig et al.

(10) Patent No.: US 12,558,032 B2
(45) Date of Patent: Feb. 24, 2026

(54) WEARABLE COMPUTING DEVICE HAVING A CONTROL CIRCUIT TO DETECT AGGRESSORS AFFECTING PHOTOPLETHYSMOGRAPHY (PPG) DATA

(71) Applicant: Google LLC, Mountain View, CA (US)

(72) Inventors: Sachin Prakash Nadig, San Francisco, CA (US); Isaac Chase Novet, Escondido, CA (US)

(73) Assignee: GOOGLE LLC, Mountain View, CA (US)

( * ) Notice: Subject to any disclaimer, the term of this patent is extended or adjusted under 35 U.S.C. 154(b) by 162 days.

(21) Appl. No.: 18/315,260

(22) Filed: May 10, 2023

(65) Prior Publication Data

US 2024/0374216 A1     Nov. 14, 2024

(51) Int. Cl.
*A61B 5/00* (2006.01)
*A61B 5/024* (2006.01)

(52) U.S. Cl.
CPC ........ *A61B 5/7214* (2013.01); *A61B 5/02416* (2013.01); *A61B 5/681* (2013.01); *A61B 5/7228* (2013.01); *A61B 2562/046* (2013.01)

(58) Field of Classification Search
CPC ... A61B 5/7214; A61B 5/02416; A61B 5/721; A61B 5/7207; A61B 5/7228
See application file for complete search history.

(56) References Cited

U.S. PATENT DOCUMENTS

| | | | | |
|---|---|---|---|---|
| 6,009,317 A | * | 12/1999 | Wynn | H03D 7/168 |
| | | | | 455/116 |
| 6,363,269 B1 | | 3/2002 | Hanna et al. | |
| 2006/0058683 A1 | * | 3/2006 | Chance | A61B 5/6834 |
| | | | | 600/407 |
| 2014/0243622 A1 | * | 8/2014 | Crowe | A61B 5/02416 |
| | | | | 600/479 |

(Continued)

OTHER PUBLICATIONS

Chance et al., "Phase Measurement of Light Absorption and Scatter in Human Tissue", Review of Scientific Instruments, American Institute of Physics, vol. 69, No. 10, Oct. 1998, 26 pages.

(Continued)

*Primary Examiner* — Serkan Akar
*Assistant Examiner* — Tommy T Ly
(74) *Attorney, Agent, or Firm* — DORITY & MANNING, P.A.

(57) ABSTRACT

A wearable computing device includes a PPG sensor that includes an emitter configured to output a light signal that is modulated with a carrier signal to generate a modulated light signal. The PPG sensor further includes one or more detectors configured to receive a first reflected light signal that is a reference signal of the modulated light signal without PPG data in the carrier signal and a second reflected light signal that is a reference signal of the modulated light signal with PPG data in the carrier signal. The wearable computing device further includes a control circuit configured to synchronously demodulate the first and second instances of the modulated light signal to obtain a first demodulated signal (Continued)

Artery
218

Skin
216

Optical Window
208

214 ~ | ~ 210 | ~ 220

Emitter
200

206

First Detector
212

Second Detector
222

172 ~

~ 204

~ 210

~ 220

Driver Circuit
202

First Amplifier
224

Second Amplifier
226

~ 228

~ 230 and a second demodulated signal, respectively. The control circuit is further configured to generate data indicative of one or more aggressors affecting the PPG data based on the first and second demodulated signals.

18 Claims, 7 Drawing Sheets

(56) References Cited

U.S. PATENT DOCUMENTS

| | | | |
|---|---|---|---|
| 2015/0190063 A1 | 7/2015 | Zakharov et al. | |
| 2019/0246963 A1* | 8/2019 | Chung | A61B 5/14532 |
| 2020/0004336 A1 | 1/2020 | Newberry | |
| 2020/0205677 A1 | 7/2020 | Ito et al. | |
| 2023/0081751 A1* | 3/2023 | Chatham | A61B 5/681 |
| | | | 600/479 |

OTHER PUBLICATIONS

International Search Report and Written Opinion for Application No. PCT/US2024/028361, mailed Aug. 5, 2024, 18 pages.
International Preliminary Report on Patentability for Application No. PCT/US2024/028361, mailed Nov. 20, 2025, 12 pages.

* cited by examiner

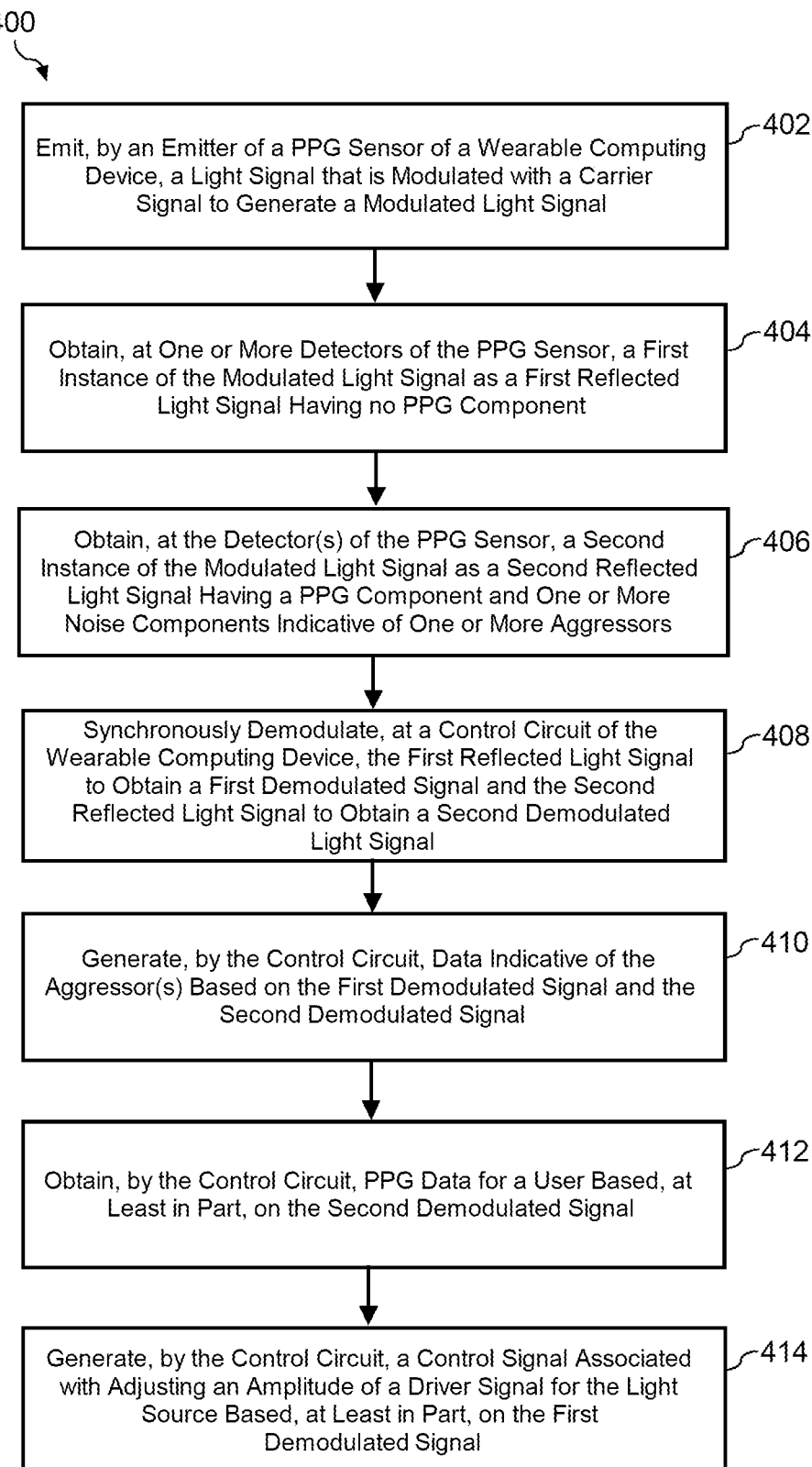

400

Emit, by an Emitter of a PPG Sensor of a Wearable Computing Device, a Light Signal that is Modulated with a Carrier Signal to Generate a Modulated Light Signal ⌐402

Obtain, at One or More Detectors of the PPG Sensor, a First Instance of the Modulated Light Signal as a First Reflected Light Signal Having no PPG Component ⌐404

Obtain, at the Detector(s) of the PPG Sensor, a Second Instance of the Modulated Light Signal as a Second Reflected Light Signal Having a PPG Component and One or More Noise Components Indicative of One or More Aggressors ⌐406

Synchronously Demodulate, at a Control Circuit of the Wearable Computing Device, the First Reflected Light Signal to Obtain a First Demodulated Signal and the Second Reflected Light Signal to Obtain a Second Demodulated Light Signal ⌐408

Generate, by the Control Circuit, Data Indicative of the Aggressor(s) Based on the First Demodulated Signal and the Second Demodulated Signal ⌐410

Obtain, by the Control Circuit, PPG Data for a User Based, at Least in Part, on the Second Demodulated Signal ⌐412

Generate, by the Control Circuit, a Control Signal Associated with Adjusting an Amplitude of a Driver Signal for the Light Source Based, at Least in Part, on the First Demodulated Signal ⌐414

FIG. 7

WEARABLE COMPUTING DEVICE HAVING A CONTROL CIRCUIT TO DETECT AGGRESSORS AFFECTING PHOTOPLETHYSMOGRAPHY (PPG) DATA

FIELD

The disclosure relates generally to wearable computing devices. More particularly, the disclosure relates to wearable computing devices having a control circuit configured to detect and mitigate aggressors affecting the accuracy of PPG data.

BACKGROUND

Some wearable computing devices (e.g., wrist watches or fitness devices) can gather data regarding activities performed by the user, or regarding the user's physiological state. Such data may include data representative of the environment around the user or the user's interaction with the environment. For example, the data can include motion data regarding the user's movements and/or physiological data obtained by measuring various physiological characteristics of the user, such as heart rate, perspiration levels, and the like.

SUMMARY

Aspects and advantages of embodiments of the disclosure will be set forth in part in the following description, or can be learned from the description, or can be learned through practice of the example embodiments.

In one aspect, a wearable computing device is provided. The wearable computing device includes a PPG sensor that includes an emitter configured to output a light signal that is modulated with a carrier signal to generate a modulated light signal. The PPG sensor includes one or more detectors. The one or more detectors are configured to receive a first reflected light signal that is a reference signal of the modulated light signal without PPG data in the carrier signal. The one or more detectors are further configured to receive a second reflected light signal that is a reference signal of the modulated light signal with PPG data in the carrier signal. The wearable computing device includes a control circuit configured to synchronously demodulate the first reflected light signal and the second reflected light signal to obtain a first demodulated signal and a second demodulated signal, respectively. The control circuit is further configured to generate data indicative of one or more aggressors affecting the PPG data based, at least in part, on the first demodulated signal and the second demodulated signal.

In some implementations, the control circuit is configured to generate the data indicative of the one or more aggressors by determining a phase shift between the first demodulated signal and the second demodulated signal and generating data indicative of the phase shift.

In some implementations, the one or more aggressors comprise motion of the wearable computing device along one or more axes due, at least in part, to motion of a user wearing the wearable computing device.

In some implementations, the first demodulated signal and the second demodulated signal each include an in-phase component that includes a first periodic signal and a quadrature component that includes a second periodic signal that is phase-shifted relative to the first periodic signal.

In some implementations, the control circuit is configured to obtain the PPG data from the second demodulated signal.

For instance, in some implementations, the control circuit is configured to determine a magnitude of the second demodulated signal to obtain the PPG data. The magnitude of the second demodulated signal can correspond to the square root of the sum of the squares of the in-phase component of the second demodulated signal and the quadrature component of the second demodulated signal.

In some implementations, the control circuit is configured to determine a quadrature imbalance exists between the in-phase component of the second demodulated signal and the quadrature component of the second demodulated signal. The control circuit is further configured to correct the quadrature imbalance to generate a corrected signal. The control circuit is even further configured to obtain the PPG data based, at least in part, on the in-phase component of the corrected signal and the quadrature component of the corrected signal.

In some implementations, the quadrature imbalance includes a direct current (DC) offset, an amplitude imbalance, or a phase imbalance.

In some implementations, the control circuit is further configured to determine an adjustment to an amplitude of the light signal is needed based, at least in part, on the first demodulated signal. The control circuit is even further configured to generate one or more control signals associated with adjusting the amplitude of the light signal.

In some implementations, the control circuit is configured to provide the data indicative of the one or more aggressors as an input to a machine-learned model configured to determine accuracy of the PPG data.

In some implementations, the carrier signal includes a periodic signal.

In another aspect, a method is provided. The method includes emitting, by an emitter of a PPG sensor of a wearable computing device, a light signal that is modulated with a carrier signal to generate a modulated light signal. The method includes obtaining, by one or more detectors of the PPG sensor, a first reflected light signal that is a reference signal of the modulated light signal without PPG data in the carrier signal. The method includes obtaining, by the one or more detectors, a second reflected light signal that is a reference signal of the modulated light signal with PPG data in the carrier signal. The method includes synchronously demodulating, at a control circuit of the wearable computing device, the first reflected light signal and the second reflected light signal to obtain a first demodulated signal and a second demodulated signal respectively. The method includes generating, by the control circuit, data indicative of one or more aggressors affecting the PPG data based, at least in part, on the first demodulated signal and the second demodulated signal.

In some implementations, generating the data indicative of the one or more aggressors affecting the PPG data include determining, by the control circuit, a phase shift between the first demodulated signal and the second demodulated signal and generating, by the control circuit, the data based, at least in part, on the phase shift between the first demodulated signal and the second demodulated signal.

In some implementations, the one or more aggressors include motion of the wearable computing device along one or more axes due, at least in part, to motion of a user wearing the wearable computing device.

In some implementations, the first demodulated signal and the second demodulated signal each include an in-phase component that includes a first periodic signal and a quadrature component that includes a second periodic signal that is phase-shifted relative to the first periodic signal.

These and other features, aspects, and advantages of various embodiments of the disclosure will become better understood with reference to the following description, drawings, and appended claims. The accompanying drawings, which are incorporated in and constitute a part of this specification, illustrate example embodiments of the disclosure and, together with the description, serve to explain the related principles.

BRIEF DESCRIPTION OF THE DRAWINGS

Detailed discussion of example embodiments directed to one of ordinary skill in the art is set forth in the specification, which makes reference to the appended drawings, in which:

FIG. 7 depicts a flow diagram of a method for mitigating aggressors affecting a PPG signal according to some implementations of the present disclosure.

DETAILED DESCRIPTION

Figure 1:
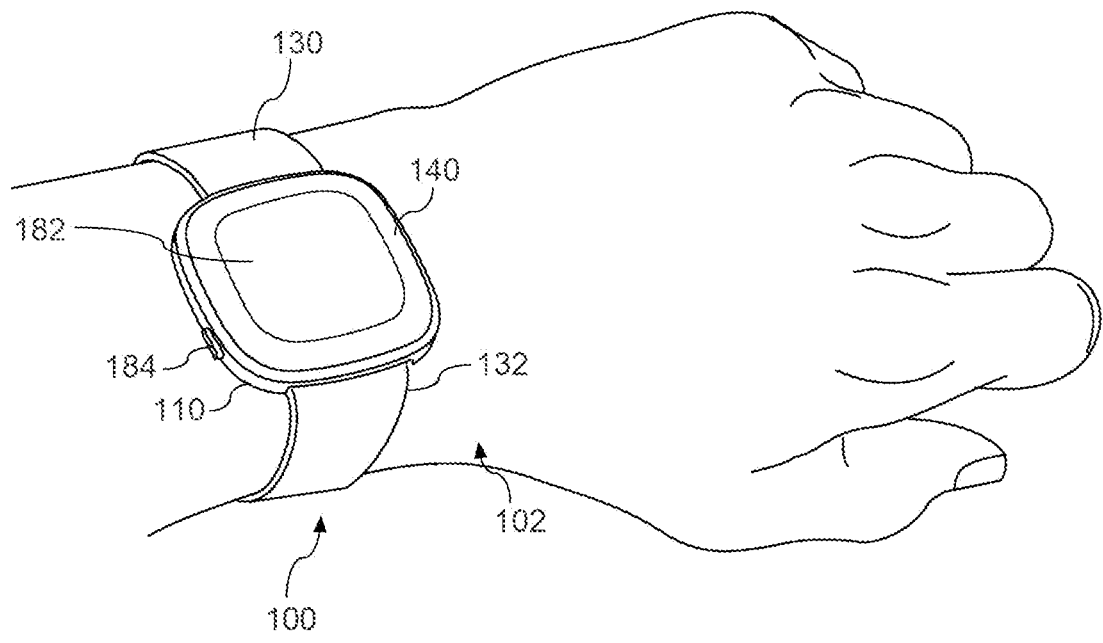
FIG. 1 depicts an example wearable computing device according to some implementations of the present disclosure.

Reference now will be made to embodiments of the disclosure, one or more examples of which are illustrated in the drawings. Each example is provided by way of explanation of the disclosure and is not intended to limit the disclosure. In fact, it will be apparent to those skilled in the art that various modifications and variations can be made to disclosure without departing from the scope or spirit of the disclosure. For instance, features illustrated or described as part of one embodiment can be used with another embodiment to yield a still further embodiment. Thus, it is intended that the disclosure covers such modifications and variations as come within the scope of the appended claims and their equivalents.

Terms used herein are used to describe the example embodiments and are not intended to limit and/or restrict the disclosure. The singular forms "a," "an" and "the" are intended to include the plural forms as well, unless the context clearly indicates otherwise. In this disclosure, terms such as "including", "having", "comprising", and the like are used to specify features, numbers, steps, operations, elements, components, or combinations thereof, but do not preclude the presence or addition of one or more of the features, elements, steps, operations, elements, components, or combinations thereof.

It will be understood that, although the terms first, second, third, etc., may be used herein to describe various elements, the elements are not limited by these terms. Instead, these terms are used to distinguish one element from another element. For example, without departing from the scope of the disclosure, a first element may be termed as a second element, and a second element may be termed as a first element.

The term "and/or" includes a combination of a plurality of related listed items or any item of the plurality of related listed items. For example, the scope of the expression or phrase "A and/or B" includes the item "A", the item "B", and the combination of items "A and B".

In addition, the scope of the expression or phrase "at least one of A or B" is intended to include all of the following: (1) at least one of A. (2) at least one of B, and (3) at least one of A and at least one of B. Likewise, the scope of the expression or phrase "at least one of A, B, or C" is intended to include all of the following: (1) at least one of A, (2) at least one of B, (3) at least one of C. (4) at least one of A and at least one of B. (5) at least one of A and at least one of C. (6) at least one of B and at least one of C, and (7) at least one of A, at least one of B, and at least one of C.

Example aspects of the present disclosure are directed to a wearable computing device that can be worn, for example, on a user's wrist. The wearable computing device includes a PPG sensor that is configured to generate a PPG signal indicative of a biometric (e.g., heart rate) of the user. The PPG sensor includes an emitter that includes one or more light sources (e.g., light emitting diodes (LEDs)) configured to emit light toward a body part of the user when the wearable computing device is worn by the user. The PPG sensor further includes one or more detectors (e.g., photodiodes) configured to receive a reflection of the light emitted toward the body part. It should be understood that the PPG signal is the reflection of the light.

The PPG signal can include a PPG component. The PPG component can include a direct current (DC) component and an alternating current (AC) component. The DC component can be indicative of the constant absorption of light passing through the tissues, whereas the AC component can be indicative of cardiac activity (e.g., heartbeats) causing volumetric changes to the user's blood.

The PPG signal can also include one or more noise components. The noise component(s) can be indicative of one or more aggressors that can affect the accuracy of the biometrics determined based, at least in part, on the PPG signal. For example, motion associated with user activity (e.g., walking, running) that causes the wearable computing device to unseat (e.g., loose contact) from the user's skin can be an aggressor affecting the accuracy of the biometrics. As another example, fluctuations in the intensity of ambient light in the surrounding environment can be an aggressor affecting the accuracy of the biometrics. Other examples of aggressors that can affect the accuracy of the biometrics determined from the PPG signal can include, without limitation, skin color of the user, dryness of the user's skin, and amount of sweat on the user's skin. It should be understood that these aggressors affecting the PPG can inhibit continuous and accurate recording of PPG data for a user. Furthermore, although backend models (e.g., machine-learned models) can be developed to remove these aggressors such models are computationally intensive and consume greater amounts of power.

Example aspects of the present disclosure are directed to wearable computing devices having a control circuit configured to detect the aggressors that affect the PPG signal. The emitter of wearable computing devices having the control circuit can emit a light signal that is modulated with a carrier signal to generate a modulated light signal. In some implementations, the carrier signal can be a periodic signal (e.g., sinusoidal). Alternatively, or additionally, a carrier frequency of the carrier signal can, in some implementations, be greater than 100 kilohertz (kHz). As will be discussed below in more detail, reflections of the modulated light signal can be synchronously demodulated at the carrier frequency to extract PPG data as well as generate data indicative of one or more aggressors affecting the accuracy of such data.

In some implementations, a first instance of the modulated light signal (e.g., first reflected light signal) can travel along a first path (e.g., light pipe) in which the light signal does not penetrate the user's skin. More specifically, the first instance of the modulated light signal traveling along the first path can reflect off an interior surface (e.g., glass window) of the wearable computing device as a first reflected light signal that is detected by one or more detectors of the PPG sensor. It should be understood that the first reflected light signal does not include a PPG component (that is, PPG data) since the first instance of the modulated light signal traveling along the first path never penetrates the user's skin and thus does not reflect off one of the user's arteries. It should also be understood that the first reflected light signal is phase-shifted by a first amount (e.g., theta1) that is indicative of a reference phase shift of the wearable computing device.

In some implementations, a second instance of the modulated light signal (e.g., second reflected light signal) can travel along a second path that is different from the first path. The modulated light signal traveling along the second path can exit the wearable computing device, penetrates the user's skin, and reflect off an artery of the user as a second reflected light signal that reenters the wearable computing device and is detected by the one or more detectors of the PPG sensor. It should be understood that the second reflected light signal includes a PPG component (that is, PPG data) from which biometrics of the user can be determined. It should also be understood that the second reflected light signal is phase-shifted by a second amount (e.g., theta2) that is different from the first amount (e.g., theta1) by which the first reflected signal is phase-shifted. This is due, at least in part, to the one or more noise components indicative of aggressors that can affect the accuracy of the biometrics determined from the PPG signal (e.g., second reflected signal).

In some implementations, the control circuit can include one or more demodulators configured to synchronously demodulate the first instance of the modulated light signal (e.g., first reflected light signal) at the carrier frequency to obtain a first demodulated signal. The one or more demodulators can be further configured to synchronously demodulate the second instance of the modulated light signal (e.g., second reflected light signal) at the carrier frequency to obtain a second demodulated signal.

In some implementations, the first demodulated signal and the second demodulated signal can each include an in-phase component and a quadrature component. The in-phase component can include that includes a first periodic signal and a quadrature component that includes a second periodic signal that is phase-shifted (e.g., by 90-degrees) relative to the first periodic signal.

It should be appreciated that demodulating the second instance of the modulated light signal (e.g., second reflected light signal) at the carrier frequency allows the PPG component (that is, PPG data) that is encoded in the carrier signal to be effectively isolated from the one or more noise components that are at frequencies (e.g., less than 100 Hz) other than the carrier frequency.

In some implementations, the control circuit can include a controller configured to generate data indicative of one or more aggressors that can affect biometrics determined based on the PPG signal (e.g., second reflected light signal). More specifically, the controller can be configured to generate data indicative of a phase shift between the first demodulated signal and the second demodulated signal. For instance, in some implementations, the phase shift can be due, at least in part, to a first aggressor, such as motion of the wearable computing device along one or more axes due, at least in part, to motion due to activity (e.g., walking, running, etc.) of a user wearing the wearable computing device.

In some implementations, the control circuit can be configured to obtain PPG data from the second demodulated signal. For instance, the control circuit can be configured to determine a magnitude of the second demodulated signal that is indicative of the PPG data. It should be appreciated that the magnitude of the second demodulated signal can correspond to the square root of the sum of squares of the in-phase component of the second demodulated signal and the quadrature component of the second demodulated signal.

In some implementations, the PPG data and the data indicative of one or more aggressors can be provided as inputs to one or more machine-learned models. In this manner, the machine-learned model(s) can learn how the aggressors affect the PPG data.

In some implementations, the controller of the control circuit can be configured to determine whether an adjustment to an amplitude of the light signal output by the emitter is needed. More specifically, the controller can be configured to determine a magnitude of the first demodulated signal. The controller can provide the determined magnitude of the first demodulated signal as an input to an automatic gain control loop (e.g., proportional integral (PI) controller) of the control circuit. The automatic gain control loop can determine based, at least in part, on the input (that is, the magnitude of the first demodulated signal) whether the amplitude of the light signal output by the emitter needs to be adjusted (e.g. increased or decreased). Furthermore, if the amplitude of the light signal needs to be generated, the amplitude gain control loop can output a control signal associated with adjusting the amplitude of the light signal as needed.

It should be appreciated that the amount by which the amplitude of the light signal needs to be adjusted according to the control signal can be indicative of an air gap between the user's skin and the wearable computing device along an axis (e.g., vertical axis). It should also be appreciated that the automatic gain control loop of the control circuit can ensure operation of the emitter is controlled so as to conserve power. For instance, the automatic gain control loop can increase the amplitude of the light signal when the air gap between the user's skin and the wearable computing device increases. Alternatively, the automatic gain control loop can decrease the amplitude of the light signal when the air gap between the user's skin and the wearable computing device decreases.

Wearable computing devices having a control circuit according to example aspects of the present disclosure can provide numerous technical effects and benefits. For instance, modulating the light signal output by the emitter with a carrier signal at a carrier frequency (e.g., greater than 100 kHz) needed to lessen the impact of one or more noise components included in a PPG signal and indicative of one or more aggressors affecting biometric determined from the PPG component thereof. In this manner, biometrics determined based, at least in part, on the isolated PPG component can be more accurate compared to biometrics determined by conventional wearable computing devices having PPG sensors. Furthermore, data indicative of the one or more aggressors can be generated and provided as an input to one or more machine-learned models configured to determine accuracy of PPG data obtained from the PPG sensor. In this manner, the complexity of the machine-learned models can be reduced, which can result in improved performance (e.g., less computing resources, improved battery life, etc.) of the wearable computing device.

Figure 2:
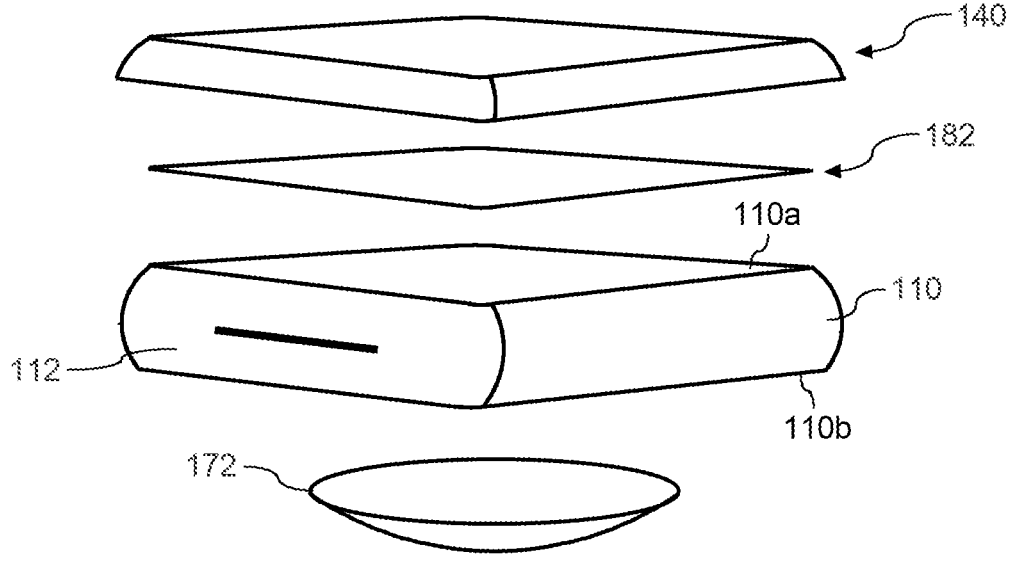
FIG. 2 depicts an exploded view of an example wearable computing device according to some implementations of the present disclosure.
Figure 3:
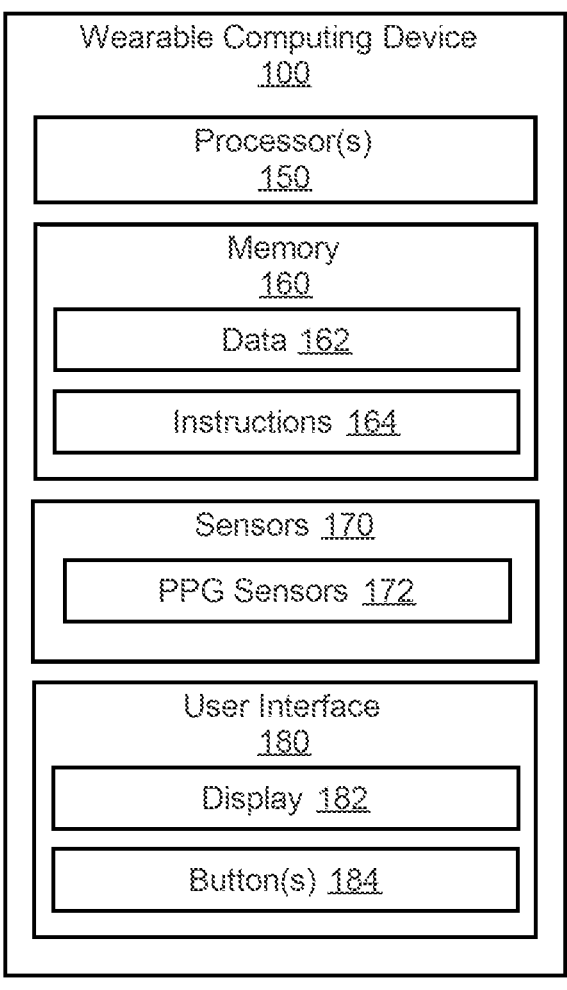
FIG. 3 depicts an example block diagram of the wearable computing device according to some implementations of the present disclosure.

Referring now to the drawings, FIGS. 1 through 3 illustrate examples of a wearable computing device 100 according to various examples of the disclosure. The wearable computing device 100 can be worn, for example, on a body part 102 (e.g., an arm, wrist, etc.) of a user. The wearable computing device 100 includes a body 110 having an upper part 110*a* and a lower part 110*b*. Furthermore, the body 110 defines a cavity 112 in which one or more electronic components (e.g., disposed on one or more printed circuit boards) are disposed. The wearable computing device 100 includes a printed circuit board (not shown) disposed within the cavity 112. Furthermore, one or more electronic components are disposed on the printed circuit board. The wearable computing device 100 can further include a battery that is disposed within the cavity 112 defined by the body 110. The wearable computing device 100 further includes various sensors 170 that are disposed within the cavity 112 defined by the body 110. For example, the sensors 170 may include one or more photoplethysmography (PPG) sensors 172 disposed at the lower part 110*b* of the body 110. The PPG sensor(s) 172 can, for example, be used to monitor a heart rate of the user. The PPG sensor(s) 172 include one or more emitters (e.g., light-emitting diodes (LEDs)) and a plurality of detectors (e.g., photodiodes).

Light emitted from the one or more emitters is transmitted in a direction toward the user's body part (e.g., a portion of a user's wrist) which is in contact with the lower part 110*b* of the body 110. The light then interacts with blood vessels of the user, where it is modified to a degree that is influenced by the current blood volume in the blood vessels. The modified light is directed back toward the PPG detectors by reflection and/or refraction. The PPG detectors generate data (e.g., one or more signals) which is reflective of the current blood volume of the blood vessels of the user which received the light emitted from the one or more emitters.

In FIG. 1 the wearable computing device 100 includes a first band 130 and a second band 132. As shown, the first band 130 is coupled to the body 110 at a first location thereon. Conversely, the second band 132 is coupled to the body 110 at a second location thereon. Furthermore, the first band 130 and the second band 132 can be coupled to one another to secure the body 110 to the body part 102 of the user.

In some examples, the first band 130 can include a buckle or clasp (not shown). Additionally, the second band 132 can include a plurality of apertures (not shown) spaced apart from one another along a length of the second band 132. In such implementations, a prong of the buckle associated with the first band 130 can extend through one of the plurality of openings defined by the second band 132 to couple the first band 130 to the second band 132. It should be appreciated that the first band 130 can be coupled to the second band 132 using any suitable type of fastener. For example, in an embodiment, the first band 130 and the second band 132 can include a magnet. In such implementations, the first band 130 and the second band 132 can be magnetically coupled to one another to secure the body 110 to a body part 102 (e.g., an arm) of the user.

In FIG. 1, the wearable computing device 100 includes a cover 140 positioned on the body 110 so that the cover 140 is positioned on top of a display 182. In this manner, the cover 140 can protect the display 182 from being scratched. In an embodiment, the wearable computing device 100 can include a seal (not shown) positioned between the body 110 and the cover 140. For instance, a first surface of the seal can contact the body 110 and a second surface of the seal can contact the cover 140. In this manner, the seal between the body 110 and the cover 140 can prevent a liquid (e.g., water) from entering the cavity 112 defined by the body 110.

It should be understood that the cover 140 can be optically transparent so that the user can view information being displayed on the display 182. For instance, in an embodiment, the cover 140 can include a glass material. It should be understood, however, that the cover 140 can include any suitable optically transparent material.

FIG. 3 illustrates an example block diagram of the wearable computing device 100 according to one or more example embodiments of the disclosure. In FIG. 3, the wearable computing device 100 includes one or more processors 150, one or more memory devices 160, one or more sensors 170, and a user interface 180.

For example, the one or more processors 150 can be any suitable processing device that can be included in a wearable computing device 100. For example, such a processor 150 may include one or more of a processor, processor cores, a controller and an arithmetic logic unit, a central processing unit (CPU), a graphics processing unit (GPU), a digital signal processor (DSP), an image processor, a microcomputer, a field programmable array, a programmable logic unit, an application-specific integrated circuit (ASIC), a microprocessor, a microcontroller, etc., and combinations thereof, including any other device capable of responding to and executing instructions in a defined manner. The one or more processors 150 can be a single processor or a plurality of processors that are operatively connected, for example in parallel.

The one or more memory devices 160 can include one or more non-transitory computer-readable storage mediums, such as such as a Read Only Memory (ROM), Programmable Read Only Memory (PROM), Erasable Programmable Read Only Memory (EPROM), and flash memory, a USB drive, a volatile memory device such as a Random Access Memory (RAM), a hard disk, floppy disks, a blue-ray disk, or optical media such as CD ROM discs and DVDs, and combinations thereof. However, examples of the one or more memory devices 160 are not limited to the above description, and the one or more memory devices 160 may be realized by other various devices and structures as would be understood by those skilled in the art.

The one or more memory devices 160 can include data 162 and instructions 164 that can be retrieved, manipulated, created, or stored by the one or more processor(s) 150.

In FIG. 3, the wearable computing device 100 includes a user interface 180 configured to receive an input from a user (e.g., via a touch input such as a thumb, finger, or an input device such as a stylus or pen). The wearable computing device 100 may execute a function in response to receiving the input from the user (e.g., checking health information about the user such as a blood pressure, making and/or receiving a phone call, sending and/or receiving a text message, obtaining a current time, setting a timer, a stopwatch function, controlling an external device such as a home appliance, and the like).

In FIG. 3, the user interface 180 includes the display 182 which displays information viewable by the user (e.g., time, date, biometric information, notifications, etc.). For example, the display 182 may be a non-touch sensitive display or a touch-sensitive display. The display 182 may include a liquid crystal display (LCD), a light emitting diode (LED) display, an organic light emitting diode (OLED) display, active matrix organic light emitting diode (AMO-LED), flexible display, 3D display, a plasma display panel (PDP), a cathode ray tube (CRT) display, and the like, for example. However, the disclosure is not limited to these example displays and may include other types of displays. The display 182 may have a square or rectangular shape, or may be annular in shape (e.g., elliptical, circular, etc.). However, the shape of the display 182 is not limited thereto.

The user interface 180 may additionally, or alternatively, include one or more buttons 184 to receive an input from a user by the user applying a force to the button 184. The button 184 may be included on one or more peripheral sides of the wearable computing device 100 as shown in FIG. 1, for example. The button 184 may include mechanical components and/or electrical circuitry to implement a function of the wearable computing device 100 (e.g., setting a time, changing a setting and/or view of the display 182, selecting an option displayed on the display 182).

Figure 4A:
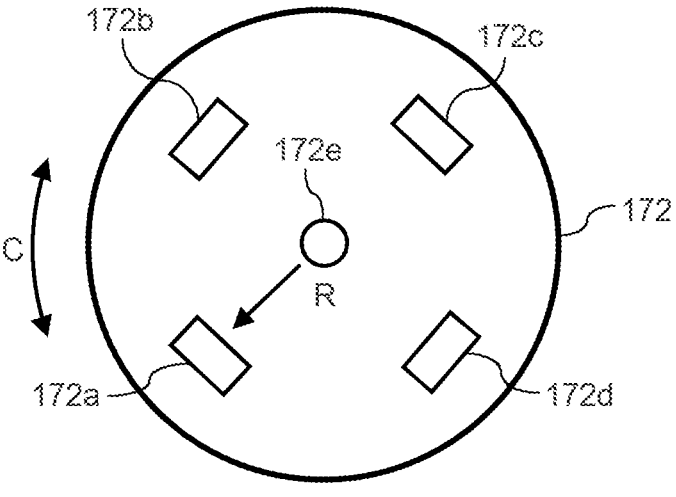
FIGS. 4A and 4B depict a bottom view of example wearable computing devices according to one or more example embodiments of the disclosure.

Referring now to FIG. 4A, a bottom view of an example wearable computing device is illustrated according to one or more example embodiments of the disclosure. The wearable computing device may include a plurality of PPG sensors, for example to assist in rejecting motion artifacts. Each PPG sensor may correspond to a combination of one or more light sources and one or more detectors. For example, the wearable computing device may include two or more PPG sensors. Furthermore, more than one light source (e.g., a LED) may be included such that different detectors may be combined with different LEDs and/or each detector may be combined with one or more LEDs to output a respective PPG signal. For example, the plurality of detectors may be disposed in a circular or elliptical arrangement, where the plurality of detectors may be spaced apart from each other at regular or irregular intervals. In FIG. 4A, light source (e.g. LED) 172e is disposed in a central portion of the PPG sensor 172. Detector 172a is spaced apart from detectors 172b and 172d along a circumferential direction C, and is spaced apart from the light source (e.g. LED) 172e in a radial direction R. Likewise, each of detectors 172b, 172c, and 172d is spaced apart from adjacent detectors in the circumferential direction C, and is spaced apart from the light source (e.g., LED) 172e in a radial direction R. However, the configuration of the detectors and light source may be different from that illustrated in FIG. 4A, and the disclosure is not limited to the example of FIG. 4A.

Figure 4B:
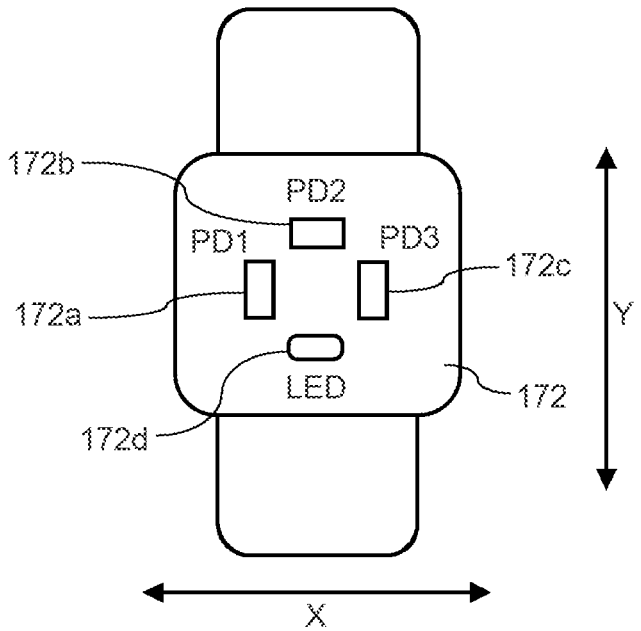

Referring now to FIG. 4B, a bottom view of another example wearable computing device is illustrated according to one or more example embodiments of the disclosure. For example, in FIG. 4B detector 172a is spaced apart from detector 172c in the horizontal or "X" direction, and is spaced apart from detector 172b in both the horizontal (X) direction and the vertical or "Y" direction. Detector 172b is spaced apart from both detectors 172a and 172c in the horizontal (X) direction and vertical (Y) direction. Detector 172c is spaced apart from detector 172a in the horizontal (X) direction and is spaced apart from detector 172b in both the horizontal (X) direction and the vertical (Y) direction. Light source (e.g. LED) 172e is spaced apart from detector 172b in the vertical (Y) direction and is spaced apart from both detectors 172a and 172c in each of the horizontal (X) and vertical (Y) directions. However, the configuration of the detectors and light source may be different from that illustrated in FIG. 4B, and the disclosure is not limited to the example of FIG. 4B.

Figure 5:
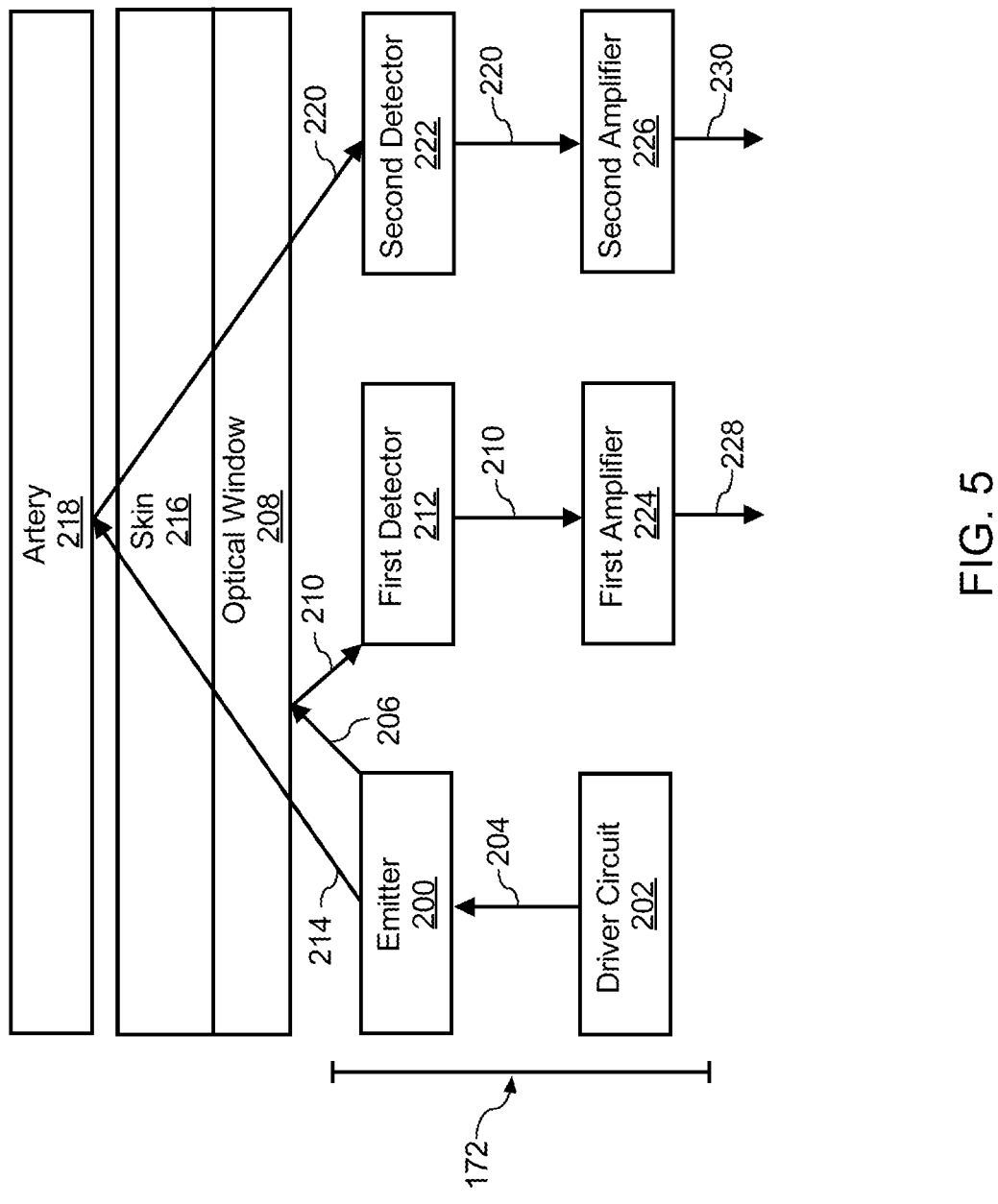
FIG. 5 illustrates components of a PPG sensor according to some implementations of the present disclosure.

Referring now to FIG. 5, the PPG sensor 172 is provided according to some implementations of the present disclosure. As shown, the PPG sensor 172 includes an emitter 200. In some implementations, the emitter 200 can include one or more LEDs configured to emit a light signal that is modulated with a carrier signal (e.g., periodic signal) at a carrier frequency (e.g., greater than 100 kHz). Furthermore, the PPG sensor 172 can include a driver circuit 202 configured to emit a driver signal 204 to adjust (e.g., increase or decrease) an amplitude of the light signal.

In some implementations, a first instance 206 of the modulated light signal (e.g., first reflected light signal 206) can travel along a first path (e.g., light pipe) and reflect off an interior surface of the body 110 (FIG. 1) of the wearable computing device 100. For instance, the first instance 206 of the modulated light signal can reflect off an optical window 208 that is part of the lower part 110b (FIG. 2) of the body 110. As shown, the first instance 206 of the modulated light signal can reflect off the optical window 208 as a first reflected light signal 210 that is detected by a first detector 212 (e.g., photodiode) of the PPG sensor 172.

In some implementations, the first reflected light signal 210 can be a sinusoidal signal. For instance, the sinusoidal signal can be A(t) sin sin (wt+Θ1) in which "A" corresponds to the changing amplitude of the modulated light signal due to non-idealities of the wearable computing device 100. Additionally, Θ1 can correspond to the phase shift of the carrier signal due, at least in part, to the wearable computing device 100, specifically the optical window 208 thereof.

In some implementations, a second instance 214 of the modulated light signal (e.g., second reflected light signal 214) can exit the cavity 112 (FIG. 2) defined by the body 110 (FIG. 2) of the wearable computing device 100. More specifically, the second instance 214 of the modulated light signal can pass through the optical window 208 that is part of the body 110 and penetrate skin 216 of the user wearing the wearable computing device 100. The second instance 214 of the modulated light signal can reflect off an artery 218 of the user as a second reflected light signal 220 that reenters the cavity 112 defined by the body 110 of the wearable computing device 100 and is detected by a second detector 222 (e.g., photodiode) of the PPG sensor 172.

It should be appreciated that the first reflected light signal 210 does not include a PPG component since the first instance 206 of the modulated light signal reflects off an interior surface (e.g., optical window 208) of the body 110 of the wearable computing device 100. Conversely, it should be appreciated that the second reflected light signal 220 does include a PPG component since the second instance 214 of the modulated light signal reflects off the artery 218 of the user. Thus, the second reflected light signal 220 can be considered a PPG signal.

In some implementations, the second reflected light signal 220 can be a sinusoidal signal. For instance, the sinusoidal signal can be a sinusoidal signal having a PPG component and one or more noise components associated with aggressors (e.g., motion, fluctuations in ambient light, skin color, dryness of skin, etc.) affecting the accuracy of biometric determined from the second reflected light signal 220 (that is, PPG signal). The PPG component can be modeled as $V_{ppg(t)}$*sin (wt+Θ2) in which Vppg(t) corresponds to PPG signal and Θ2 refers to the phase shift of the carrier signal.

It should be appreciated that the difference between the phase shift, Θ2, of the carrier signal associated with the second reflected light signal 220 (e.g., PPG signal) and the phase shift, Θ1, associated with the first reflected light signal (e.g., reference signal) can be indicative of the phase shift due, at least in part, to the one or more aggressors. It should also be appreciated that the one or more noise components associated with aggressors affecting the PPG signal can be direct current components and thus have no frequency component. Alternatively, the one or more noise components can occur at a frequency that is different from (e.g., less than 100 Hz) the carrier frequency associated with the carrier signal in which the PPG component is encoded.

In some implementations, the wearable computing device 100 can include one or more amplifiers configured to receive the reflected light signals (e.g., first reflected light signal 210 and second reflected light signal 220) from the detectors (e.g., first detector 212, second detector 222). For instance, in some implementations, the wearable computing device 100 can include a first amplifier 224 configured to receive the first reflected light signal 210 from the first detector 212 and a second amplifier 226 configured to receive the second reflected light signal 220 from the second detector 222. The first amplifier 224 can be configured to amplify the first reflected light signal 210 to generate a first amplified signal 228. The second amplifier can be configured to amplify the second reflected light signal 220 to generate a second amplified signal 230.

It should be appreciated that the first amplifier 224 and the second amplifier 226 can include any suitable type of amplifier. For instance, in some implementations, at least one of the first amplifier 224 or the second amplifier 226 can include a transimpedance amplifier. It should also be appreciated that, in some implementations, a single amplifier can be used to amplify both the first reflected light signal 210 and the second reflected light signal 220.

It should be appreciated that the PPG sensor 172 can, in alternative implementations, include more or fewer emitters and detectors. For instance, in some implementations, the PPG sensor 172 can include two or more emitters. More specifically, the PPG sensor 172 can include a first emitter configured to emit a light signal at a wavelength associated with green light and a second emitter configured to emit a light signal at a wavelength associated with red light. Furthermore, in some implementations, the emitter 200 can be configured to emit light at wavelength associated with infrared light. Alternatively, or additionally, the PPG sensor 172 can, in some implementations, include a single detector configured to detect both the first reflected light signal 210 and the second reflected light signal 220.

Figure 6:
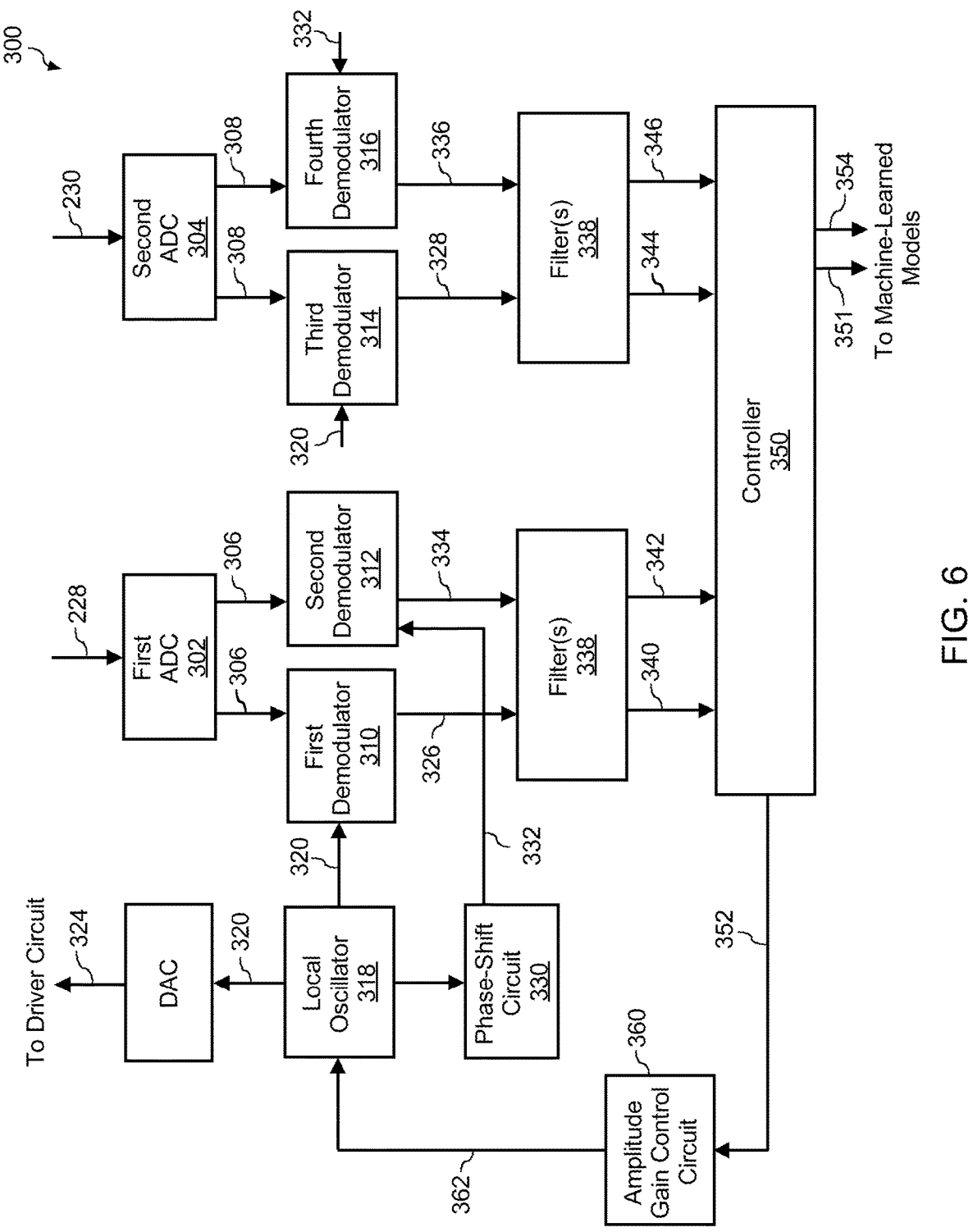
FIG. 6 depicts a control circuit for mitigating aggressors affecting a PPG signal according to some implementations of the present disclosure.

Referring now to FIG. 6, a block diagram of components of a control circuit 300 for detecting aggressors affecting the PPG signal of a PPG sensor of a wearable computing device is provided according to some implementations of the present disclosure. For instance, the control circuit 300 can be used in conjunction with the PPG sensor 172 discussed above with reference to FIG. 5. It should be appreciated, however, that the control circuit 300 can be used with any suitable PPG sensor having one or more emitters (e.g., LED) and one or more detectors.

In some implementations, the control circuit 300 can include a first analog-to-digital converter (ADC) 302 and a second ADC 304. The first ADC 302 can be configured to receive the first amplified signal 228 from the first amplifier 224 (FIG. 5). The second ADC 304 can be configured to receive the second amplified signal 230 from the second amplifier 226 (FIG. 5). It should be appreciated that, in alternative implementations, the first reflected light signal 210 and the second reflected light signal 220 can be provided to the first ADC 302 and second ADC 304 without first being amplified. As shown, the first ADC 302 can be configured to convert the first amplified signal 228 into a first digital signal 306. Furthermore, the second ADC 304 can be configured to convert the second amplified signal 230 into a second digital signal 308.

In some implementations, the control circuit 300 can include a first demodulator 310 and a second demodulator 312 configured to receive the first digital signal 306 output by the first ADC 302. In this manner, the first demodulator 310 and the second demodulator 312 can demodulate the first digital signal 306 to obtain a first demodulated signal. Furthermore, the control circuit 300 can include a third demodulator 314 and a fourth demodulator 316 configured to receive the second digital signal 308 output by the second ADC 304. In this manner, the third demodulator 314 and the fourth demodulator 316 can demodulator the second digital signal 308 to obtain a second demodulated signal.

In some implementations, the control circuit 300 can include a local oscillator 318 configured to generate a local oscillator signal 320 at the carrier frequency (e.g., 100 kHz). The control circuit 300 can further include a digital to analog converter (DAC) 322 configured to receive the local oscillator signal 320 from the local oscillator 318. The DAC 322 can be configured to convert the local oscillator signal from a digital signal to an analog signal 324 that is provided as an input to the driver circuit 202 (FIG. 5) of the PPG sensor 172 to control modulation of the amplitude of the light signal emitted by the emitter 200 (FIG. 5) of the PPG sensor 172.

The local oscillator signal 320 can also be provided as an input to the first demodulator 310. In this manner, the first demodulator 310 can demodulate the first digital signal 306 to obtain a first component 326 (e.g., in-phase component including a first periodic signal) thereof. The local oscillator signal 320 can also be provided as an input to the third demodulator 314. In this manner, the third demodulator 314 can demodulate the second digital signal 308 to obtain a first component 328 (e.g., in-phase component including a first periodic signal) thereof.

In some implementations, the control circuit 300 can include a phase-shifter circuit 330 configured to receive the local oscillator signal 320 from the local oscillator 318 and generate a phase-shifted local oscillator signal 332 that is provided as an input to the second demodulator 312 and the fourth demodulator 316. For instance, in some implementations, the phase-shifter circuit 330 can be configured to shift a phase of the local oscillator signal 320 by 90 degrees. In this manner, a phase-difference between a phase of the local oscillator signal 320 and a phase of the phase-shifted local oscillator signal 332 can be 90 degrees.

The second demodulator 312 can be configured to demodulate the first digital signal 306 to obtain a second component 334 (e.g., quadrature component including a second periodic signal that is phase-shifted relative to the first periodic signal) thereof. Likewise, the fourth demodulator 316 can be configured to demodulate the second digital signal 308 to obtain a second component 336 (e.g., quadrature component including a second periodic signal that is phase-shifted relative to the first periodic signal) thereof.

It should be appreciated that the first component 326 (e.g., in-phase component including a first periodic signal) output by the first demodulator 310 and the second component 334 (e.g., quadrature component including a second periodic signal that is phase-shifted relative to the first periodic signal of the first component) output by the second demodulator 312 can collectively be referred to as a first demodulated signal associated with the first reflected light signal 210 (FIG. 5). It should also be appreciated that the first component 328 (e.g., in-phase component including a first periodic signal) output by the third demodulator 314 and the second component 336 (e.g., quadrature component including a second periodic signal that is phase-shifted relative to the first periodic signal) output by the fourth demodulator 316 can collectively be referred to as a second demodulated signal associated with the second reflected light signal 220 (FIG. 5).

In some implementations, the control circuit 300 can include one or more filters 338 configured to receive the first demodulated signal and the second demodulated signal. For instance, in some implementations, the control circuit 300 can include a first filter (e.g., low-pass filter) configured to receive the first component 326 of the first demodulated signal. In this manner, the first filter can filter the first component 326 of the first demodulated signal to obtain a first filtered signal 340. The control circuit 300 can further include a second filter (e.g., low-pass filter) configured to receive the second component 334 of the first demodulated signal. In this manner, the second filter can filter the second component 334 of the first demodulated signal to obtain a second filtered signal 342.

In some implementations, the control circuit can include a third filter (e.g., low-pass filter) configured to receive the first component 328 of the second demodulated signal. In this manner, the third filter can filter the first component 328 of the second demodulated signal to obtain a third filtered signal 344. The control circuit 300 can further include a fourth filter (e.g., low-pass filter) configured to receive the second component 336 of the second demodulated signal. In this manner, the second filter can filter the second component 336 of the second demodulated signal to obtain a fourth filtered signal 346.

In some implementations, the control circuit 300 can include a controller 350. In some implementations, the controller 350 can be implemented as an application specific integrated circuit. In alternative implementations, the controller 350 can include one or more processors. For instance, in some implementations, the controller 350 can include the one or more processors 150 of the wearable computing device 100 discussed above with reference to FIG. 3.

The controller 350 can be configured to obtain PPG data 351 for the user based, at least in part, on the second demodulated signal (e.g., first component 328 and second component thereof 336). More specifically, the controller 350 can be configured to obtain the PPG data 351 without the one or more noise components associated with the aggressors based, at least in part, on the following equation:

$$PPG\ Data = sqrt(X1^2 + Y1^2) \qquad \text{Equation 1}$$

In the above equation (that is, Equation 1), X1 refers to the first component 328 of the second demodulated signal and Y1 refers to the second component 336 of the second demodulated signal. It should be appreciated that the one or more noise components associated with the aggressors are negligible or non-existent in the second demodulated signal since the second digital signal 308 is demodulated at the carrier frequency (e.g., greater than 100 kHz) and the noise components are at direct current (e.g., have no frequency) or at frequencies significantly lower (e.g., less than 100 Hz) than the carrier frequency.

In some implementations, the controller 350 can be configured to determine a quadrature imbalance exists between the first component 328 of the second demodulated signal and the second component 336 of the second demodulated signal. It should be understood that the quadrature imbalance can include a DC offset, an amplitude imbalance, or a phase imbalance. Furthermore, the controller 350 can be configured to generate a corrected signal in which the quadrature imbalance between the first component 328 and the second component 336 has been removed. Furthermore, in such implementations, the controller 350 can be configured to obtain the PPG data 351 from the corrected signal.

The controller 350 can be further configured to determine a magnitude of the first demodulated signal and control operation of the emitter 200 (FIG. 5) of the PPG sensor based, at least in part, the magnitude thereof. The controller 350 can be configured to determine the magnitude of the first demodulated signal based, at least in part, on the following equation.

$$R1 = sqrt(X1^2 + Y1^2) \qquad \text{Equation 2}$$

In the above equation (that is, Equation 2), X1 refers to the first component 326 of the first demodulated signal and Y1 refers to the second component 334 of the first demodulated signal.

In some implementations, the controller 350 can be configured to determine a quadrature imbalance exists between the first component 326 of the first demodulated signal and the second component 328 of the first demodulated signal. It should be understood that the quadrature imbalance can include a DC offset, an amplitude imbalance, or a phase imbalance. Furthermore, the controller 350 can be configured to generate a corrected signal in which the quadrature imbalance between the first component 326 and the second component 328 has been removed. Furthermore, in such implementations, the controller 350 can be configured to determine the magnitude, R1, of the corrected signal.

In some implementations, the control circuit 300 can include an amplitude gain control circuit 360 configured to receive a signal 352 indicative of the magnitude, R1, of the first demodulated signal. In some implementations, the amplitude gain control circuit 360 can be a proportional integral controller. The amplitude gain control circuit 360 can be configured to determine whether the magnitude, R1, of the first demodulated signal is different (e.g., greater than or less than) the amplitude, A, of the light signal currently being emitted by the emitter 200 (FIG. 5) of the PPG sensor 172. If the magnitude, R1, of the first demodulated signal is different from the amplitude, A, of the light signal currently being emitted by the emitter 200 (FIG. 5), the amplitude gain control circuit 360 can output a signal 362 to the local oscillator 318. The signal 362 can cause the local oscillator 318 to adjust the local oscillator signal 320 as needed to cause the driver circuit 202 to drive the emitter 200 as needed to bring the difference between the magnitude, R1, of the first demodulated signal and the amplitude, A, of the light signal currently being emitted by the emitter 200 to zero.

It should be appreciated that the adjustments to the local oscillator signal 320 can cause the driver circuit 202 (FIG. 5) to drive the emitter 200 (also FIG. 5) harder (e.g., increased amplitude) or softer (e.g., decreased amplitude). In this manner, the intensity of light emitted by the emitter 200 can be adjusted depending on, for instance, whether there is an air gap between the body 110 (FIG. 2) of the wearable computing device 100 and the skin 216 (FIG. 5) of the user due, at least in part, to the wearable computing device 100 unseating (e.g., loosing contact with) from the skin 216 of the user as a result of the user engaging in an activity (e.g., walking, running, etc.) that is a known aggressor affecting the accuracy of biometrics determined from the PPG signal (e.g., second reflected light signal 220) generated by the PPG sensor 172.

In some implementations, the controller 350 can be configured to generate data indicative of the one or more aggressors (e.g., motion) affecting the PPG signal (e.g., second reflected light signal 220). For instance, the controller 350 can be configured to generate data indicative of the aggressor according to the following equation.

$$\text{Aggressor} = \Theta 1 - \Theta 2 \qquad\qquad \text{Equation 3}$$

In the above equation (that is, Equation 3), $\Theta 1$ refers to the phase-shift associated with the first demodulated signal that corresponds to the arctangent of the second component 334 (e.g., quadrature component) thereof divided by the first component 326 (e.g., in-phase component) thereof. Additionally, $\Theta 2$ refers to the phase-shift associated with the second demodulated signal that corresponds to the arctangent of the second component 336 (e.g., quadrature component) thereof divided by the first component 328 thereof.

In some implementations, the controller 350 can be configured to output data 354 indicative of the aggressor to one or more machine-learned models configured to determine the accuracy of PPG data obtained using the PPG sensor. In this manner, data quantifying aggressors affecting the PPG data can be provided as an input to the one or more machine-learned models. Also, other inputs used by the machine-learned models to quantify such aggressors are no longer needed since the control circuit 300 can quantify such aggressors. In this manner, the complexity of the machine-learned models can be reduced. In some implementations, the PPG data 351 obtained from the second demodulated signal can also be provided as an input to the one or more machine-learned models.

Referring now to FIG. 7, a flow diagram of a method 400 for mitigating aggressors affecting a PPG signal generated by a PPG sensor of a wearable computing device is provided according to some implementations of the present disclosure. The method 400 may be implemented using, for instance, the control circuit 300 discussed above with reference to FIG. 6. FIG. 7 depicts steps performed in a particular order for purposes of illustration and discussion. Those of ordinary skill in the art, using the disclosures provided herein, will understand that various steps of the method 400 may be adapted, modified, rearranged, performed simultaneously or modified in various ways without deviating from the scope of the present disclosure.

At (402), the method 400 includes emitting, by an emitter of a PPG sensor of a wearable computing device, a light signal that is modulated with a carrier signal to generate a modulated light signal.

At (404), the method 400 includes obtaining, at one or more detectors of the PPG sensor, a first instance of the modulated light signal as a first reflected light signal having no PPG data encoded in the carrier signal. For instance, the first reflected light signal can be generated by the modulated light signal reflecting off an interior surface (e.g., optical window) of a body of the wearable computing device.

At (406), the method 400 includes obtaining, at the one or more detectors of the PPG sensor, the modulated light signal as a second reflected light signal having PPG data encoded in the carrier signal thereof. The second reflected light signal can also include one or more noise components indicative of aggressors affecting the accuracy of biometrics (e.g., heart-rate) determined based on the second reflected light signal. For instance, the second reflected light signal can be generated by the modulated light signal exiting the interior (e.g., cavity) of the wearable computing device, penetrating skin of the user, reflecting off an artery of the user, and reentering the interior of the wearable computing device.

At (408), the method 400 includes synchronously demodulating, at a control circuit of the wearable computing device, the first reflected light signal at the carrier frequency to obtain a first demodulated light signal and the second reflected light signal at the carrier frequency to obtain a second demodulated light signal.

At (410), the method 400 includes generating data indicative of the one or more aggressors based, at least in part, on the first demodulated signal and the second demodulated signal. For instance, the data indicative of the one or more aggressors can include data indicative of a phase shift between the first demodulated signal and the second demodulated signal. In some implementations, the phase shift can be indicative of motion of the wearable computing device along one or more axes due, at least in part, to a user wearing the wearable computing device engaging in an activity (e.g., walking, running) that causes the body of the wearable computing device to unseat (e.g., loose contact with) from the user's skin.

At (412), the method 400 can, in some implementations, include obtaining the PPG data from the second demodulated signal. For instance, in some implementations, the PPG data can be obtained by determining the magnitude of the second demodulated signal. In some implementations, the magnitude of the second demodulated signal can correspond to the square root of the sum of squares of the first and second components of the second demodulated signal.

At (414), the method 400 can, in some implementations, include generating, by the control circuit, one or more control signals associated with adjusting an amplitude of a driving signal for the light source based, at least in part, on the first demodulated signal. For instance, the one or more control signals can be associated with increasing the amplitude of the driving signal to drive the light source harder. Alternatively, the one or more control signals can be associated with decreasing the amplitude of the driving signal to drive the light source softer.

Aspects of the above-described example embodiments may be recorded in non-transitory computer-readable media including program instructions to implement various operations embodied by a computer. The media may also include, alone or in combination with the program instructions, data files, data structures, and the like. Examples of non-transitory computer-readable media include magnetic media such as hard disks, floppy disks, and magnetic tape; optical media such as CD ROM disks, Blue-Ray disks, and DVDs; magneto-optical media such as optical discs; and other hardware devices that are specially configured to store and perform program instructions, such as semiconductor memory, read-only memory (ROM), random access memory (RAM), flash memory, USB memory, and the like. Examples of program instructions include both machine code, such as produced by a compiler, and files containing higher level code that may be executed by the computer using an interpreter. The program instructions may be executed by one or more processors. The described hardware devices may be configured to act as one or more software modules in order to perform the operations of the above-described embodiments, or vice versa. In addition, a non-transitory computer-readable storage medium may be distributed among computer systems connected through a network and computer-readable codes or program instructions may be stored and executed in a decentralized manner. In addition, the non-transitory computer-readable storage media may also be embodied in at least one application specific integrated circuit (ASIC) or Field Programmable Gate Array (FPGA).

Each block of the flowchart illustrations may represent a unit, module, segment, or portion of code, which comprises one or more executable instructions for implementing the specified logical function(s). It should also be noted that in some alternative implementations, the functions noted in the blocks may occur out of order. For example, two blocks shown in succession may in fact be executed substantially concurrently (simultaneously) or the blocks may sometimes be executed in the reverse order, depending upon the functionality involved.

While the disclosure has been described with respect to various example embodiments, each example is provided by way of explanation, not limitation of the disclosure. Those skilled in the art, upon attaining an understanding of the foregoing, can readily produce alterations to, variations of, and equivalents to such embodiments. Accordingly, the disclosure does not preclude inclusion of such modifications, variations and/or additions to the disclosed subject matter as would be readily apparent to one of ordinary skill in the art. For example, features illustrated or described as part of one embodiment can be used with another embodiment to yield a still further embodiment. Thus, it is intended that the disclosure covers such alterations, variations, and equivalents.

What is claimed is:

1. A wearable computing device comprising:
   a photoplethysmography (PPG) sensor comprising:
      (i) an emitter configured to output a light signal that is modulated with a carrier signal to generate a modulated light signal; and
      (ii) one or more detectors configured to receive:
         a first reflected light signal, the first reflected light signal being a reference signal of the modulated light signal without PPG data in the carrier signal; and
         a second reflected light signal, the second reflected light signal being a reference signal of the modulated light signal with PPG data in the carrier signal; and
   a control circuit configured to:
      synchronously demodulate the first reflected light signal and the second reflected light signal to obtain a first demodulated signal and a second demodulated signal, respectively;
      generate data indicative of one or more aggressors affecting the PPG data encoded in the carrier signal based, at least in part, on the first demodulated signal and the second demodulated signal;
      determine an adjustment to an amplitude of the light signal is needed based, at least in part, on the first demodulated signal; and
      generate one or more control signals for adjusting the amplitude of the light signal.

2. The wearable computing device of claim 1, wherein to generate the data indicative of the one or more aggressors, the control circuit is configured to:
   determine a phase shift between the first demodulated signal and the second demodulated signal; and
   generate data indicative of the phase shift between the first demodulated signal and the second demodulated signal.

3. The wearable computing device of claim 1, wherein the one or more aggressors comprise motion of the wearable computing device along one or more axes due, at least in part, to motion of a user wearing the wearable computing device.

4. The wearable computing device of claim 1, wherein the first demodulated signal and the second demodulated signal each include an in-phase component comprising a first periodic signal and a quadrature component comprising a second periodic signal that is phase-shifted relative to the first periodic signal.

5. The wearable computing device of claim 4, wherein the control circuit is further configured to:
   obtain the PPG data from the second demodulated signal.

6. The wearable computing device of claim 5, wherein to obtain the PPG data, the control circuit is configured to determine a magnitude of the second demodulated signal, and wherein the magnitude of the second demodulated signal corresponds to the square root of the sum of the squares of the in-phase component of the second demodulated signal and the quadrature component of the second demodulated signal.

7. The wearable computing device of claim 5, wherein to obtain the PPG data, the control circuit is configured to:
   determine a quadrature imbalance exists between the in-phase component of the second demodulated signal and the quadrature component of the second demodulated signal;
   correct the quadrature imbalance to generate a corrected signal; and
   obtain the PPG data based, at least in part, on the in-phase component of the corrected signal and the quadrature component of the corrected signal.

8. The wearable computing device of claim 7, wherein the quadrature imbalance comprises a DC offset, an amplitude imbalance, or a phase imbalance.

9. The wearable computing device of claim 1, wherein the control circuit is further configured to:
   provide the data indicative of the one or more aggressors as an input to a machine-learned model configured to process the input and determine accuracy of the PPG data.

10. The wearable computing device of claim 1, wherein the carrier signal comprises a periodic signal.

11. A method comprising:
   emitting, by an emitter of a PPG sensor of a wearable computing device, a light signal that is modulated with a carrier signal to generate a modulated light signal;
   obtaining, by one or more detectors of the PPG sensor, a first reflected light signal, the first reflected light signal being a reference signal of the modulated light signal without PPG data in the carrier signal;
   obtaining, by the one or more detectors, a second reflected light signal, the second reflected light signal being a reference signal of the modulated light signal with PPG data in the carrier signal;
   synchronously demodulating, at a control circuit of the wearable computing device, the first reflected light signal and the second reflected light signal to obtain a first demodulated signal and a second demodulated signal, respectively;
   generating, by the control circuit, data indicative of one or more aggressors affecting the PPG data based, at least in part, on the first demodulated signal and the second demodulated signal;

determining, by the control circuit, an adjustment to an amplitude of the light signal is needed based, at least in part, on the first demodulated signal; and generating, by the control circuit, one or more control signals for making the adjustment to the amplitude of the light signal output by the emitter of the PPG sensor.

12. The method of claim 11, wherein generating the data indicative of the one or more aggressors affecting the PPG data comprises:

determining, by the control circuit, a phase shift between the first demodulated signal and the second demodulated signal; and generating the data indicative of the one or more aggressors based, at least in part, on the phase shift between the first demodulated signal and the second demodulated signal.

13. The method of claim 11, wherein the one or more aggressors comprise motion of the wearable computing device along one or more axes due, at least in part, to motion of a user wearing the wearable computing device.

14. The method of claim 11, wherein the first demodulated signal and the second demodulated signal each include an in-phase component comprising a first periodic signal and a quadrature component comprising a second periodic signal that is phase-shifted relative to the first periodic signal.

15. The method of claim 14, further comprising:

obtaining, by the control circuit, the PPG data from the second demodulated signal.

16. The method of claim 15, wherein obtaining the PPG data from the second demodulated signal comprises:

determining, by the control circuit, a magnitude of the second demodulated signal, wherein the magnitude corresponds to the square root of the sum of the squares of the in-phase component of the second demodulated signal and the quadrature component of the second demodulated signal.

17. The method of claim 14, wherein determining an adjustment to an amplitude of the light signal is needed comprises:

determining, by the control circuit, a magnitude of the first demodulated signal, wherein the magnitude corresponds to the square root of the sum of the squares of the in-phase component of the first demodulated signal and the quadrature component of the first demodulated signal; and determining, by the control circuit, the adjustment to the amplitude of the light signal is needed based, at least in part, on the magnitude of the first demodulated signal.

18. The method of claim 11, further comprising:

providing, by the control circuit, the data indicative of the one or more aggressors as an input to a machine-learned model configured to determine accuracy of the PPG data.

*     *     *     *     *